(12) United States Patent
Kim et al.

(10) Patent No.: US 10,143,651 B2
(45) Date of Patent: *Dec. 4, 2018

(54) AMPHIPHILIC POLYMER

(71) Applicants: LG Chem, Ltd., Seoul (KR); LG Household & Health Care Ltd., Seoul (KR)

(72) Inventors: Su Jeong Kim, Daejeon (KR); Jeong Ae Yoon, Daejeon (KR); Sun Hwa Lee, Daejeon (KR); Woo Sun Shim, Daejeon (KR); Sung Soo Yoon, Daejeon (KR); Chang Hwan Ju, Daejeon (KR); Jung A Kim, Daejeon (KR); Nae Gyu Kang, Daejeon (KR)

(73) Assignees: LG Chem, Ltd. (KR); LG Household & Health Care Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/355,225

(22) Filed: Nov. 18, 2016

(65) Prior Publication Data

US 2017/0143628 A1 May 25, 2017

(30) Foreign Application Priority Data

Nov. 25, 2015 (KR) .................... 10-2015-0165869

(51) Int. Cl.
*A61K 47/32* (2006.01)
*A61K 9/107* (2006.01)
*A61K 31/352* (2006.01)

(52) U.S. Cl.
CPC .......... *A61K 9/1075* (2013.01); *A61K 31/352* (2013.01); *A61K 47/32* (2013.01)

(58) Field of Classification Search
CPC ..... A61K 9/1075; A61K 47/32; A61K 31/352
See application file for complete search history.

(56) References Cited

U.S. PATENT DOCUMENTS

| 6,616,946 | B1* | 9/2003 | Meier | A61K 9/0009 424/489 |
|---|---|---|---|---|
| 2007/0253899 | A1* | 11/2007 | Ai | A61K 9/1075 424/1.37 |
| 2009/0069186 | A1* | 3/2009 | Shirley | A01N 25/30 504/360 |
| 2010/0028257 | A1* | 2/2010 | Lazzari | C07D 487/08 424/1.65 |

FOREIGN PATENT DOCUMENTS

JP 2009155282 A 7/2009

OTHER PUBLICATIONS

Miteva "Tuning PEGylation of mixed micelles to overcome intracellular and systemic siRNA delivery barriers" (Year: 2014).*
Nelson "Balancing Cationic and Hydrophobic Content of PEGylated siRNA Polyplexes Enhances Endosome Escape, Stability, Blood Circulation Time, and Bioactivity in Vivo" (Year: 2013).*

* cited by examiner

*Primary Examiner* — Robert A Wax
*Assistant Examiner* — Quanglong N Truong
(74) *Attorney, Agent, or Firm* — Lerner, David, Littenberg, Krumholz & Mentlik, LLP

(57) ABSTRACT

The present application relates to a micelle comprising a drug encapsulated by an amphiphilic polymer and a composition comprising the same. The micelle of the present application has an excellent dispersion property on an aqueous solution and a superior percutaneous absorption characteristic on preparing a formulation.

19 Claims, 1 Drawing Sheet

[Fig.1]
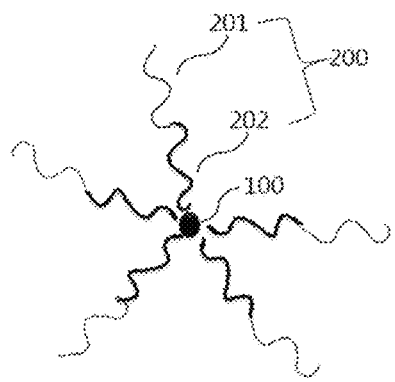
[Fig. 2]
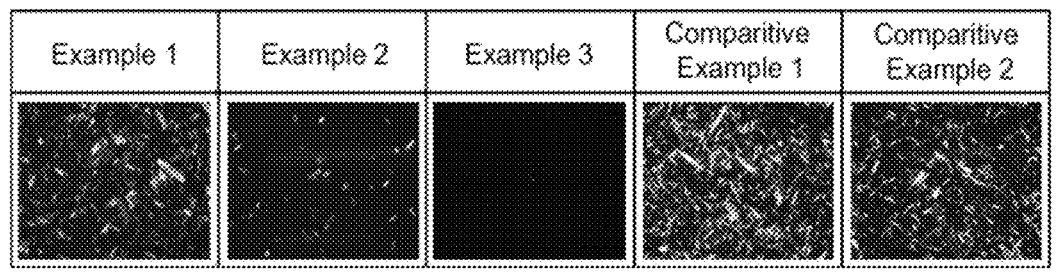
[Fig. 3]
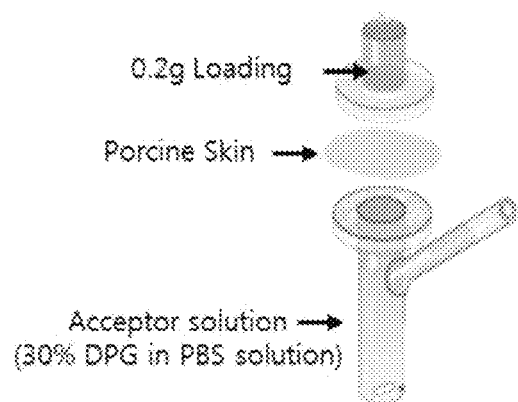

AMPHIPHILIC POLYMER

CROSS-REFERENCE TO RELATED APPLICATIONS

This application claims priority under 35 USC § 119(a) of a Korean Patent Application No. 10-2015-0165869 filed on Nov. 25, 2015, the subject matter of which is hereby incorporated by reference.

BACKGROUND

Field of the Invention

It has been required in pharmaceutical and cosmetic fields before to develop a formulation that can effectively act on the skin to improve the skin conditions, while stably loading various kinds of materials with efficacy on the skin into the product.

However, there was a problem that most of drugs are sparingly soluble or unstable so as to make the whole system unstable by combining or reacting with other materials.

Thus, various techniques for loading effective drugs into formulations more stably and also easily have been developed, and for example, nanoemulsions preparing emulsified particles by a nano unit, liposome using self-assembly characteristic of phospholipids, solid lipid nanoparticluates nano-microparticulating solid lipids or polymer type nanoparticulates stabilizing interfaces with a surfactant, and the like may be illustrated.

However, such nanoparticulates had still a difficult problem in improving a problem of poor solubility in target drugs and the percutaneous absorption effect according to the dispersion property.

Background Art

JP Laid-open Patent Publication No. 2009-155282

SUMMARY OF THE INVENTION

Technical Problem

The present application provides a micelle which is encapsulated by an amphiphilic polymer to have an excellent dispersion property and a process for preparing the same.

The present application also provides a composition comprising such micelles.

Technical Solution

The present application relates to a micelle comprising a drug which is encapsulated by an amphiphilic polymer and a process for preparing the same.

In addition, the present application relates to a composition comprising the micelles.

The present application may provide a micelle having an excellent dispersion property by effectively encapsulating a drug with a block copolymer which may represent a phase separation property using its self-assembly characteristic and also encapsulating a subject material using an amphiphilic polymer having an excellent dispersion property in a composition, where the formulation comprising these micelles may exhibit an excellent percutaneous absorption characteristic.

In the present application the term "amphiphilic polymer" may mean a polymer comprising areas having different physical properties from each other, for example different solubility parameters from each other at the same time, for example, a polymer comprising a hydrophilic area and a hydrophobic area at the same time.

In the present application the term "hydrophilic or hydrophobic area" means an area included in a polymer in a state such that it is ascertainable for each area to be phase-separated, for example, with forming a block, where each degree of hydrophilicity or hydrophobicity is relative.

In the present application the term "self-assembly characteristic" means a phenomenon that the amphiphilic polymer voluntarily causes fine phase separation in oil or in water to have a predetermined size of regularity.

The micelle of the present application comprises a drug; and an amphiphilic polymer encapsulating the drug and having a first block (A) and a second block (B) which is phase-separated with the first block (A). In addition, the second block (B) comprises a polymerization unit of an acrylic monomer or a vinylic monomer.

In the present application the term "micelle" may mean a particle of several nano to tens of thousands nano size having a core/shell structure by the self-assembly characteristic of the amphiphilic polymer.

The micelle of the present application comprising the amphiphilic polymer encapsulating the drug may have an excellent dispersion property in oil or in water, and also have an excellent stability to be effectively applied to the formulation having an excellent percutaneous absorption characteristic.

In one example, as depicted in FIG. 1, the micelle of the present application may be a structure comprising a drug (100) and an amphiphilic polymer (200) encapsulating the drug (100). In addition, the amphiphilic polymer (200) may comprise a first block (201) and a second block (202) to have a structure that the second block (202) of the amphiphilic polymer (200) is adjacent to the drug (100). The encapsulation above, as in FIG. 1, is a term meaning a structure that the amphiphilic polymer wraps around the drug, and is used in the same meaning as the "loading" herein.

Typically, the drug is sparingly soluble, but the drug of the present application may be encapsulated by the amphiphilic polymer having a hydrophobic area and a hydrophilic area at the same time to secure an excellent dispersion property of the drug in oil or in water.

In addition, in the case of the micelle of the present application, it may be effectively dispersed in oil or in water, in a state securing stability, by including the amphiphilic polymer having an excellent interaction with certain drug.

The drug contained in the micelle of the present application is not particularly limited, but may include, for example, physiologically active substances.

In one example, the physiologically active substance may be sparingly soluble.

Such a physiologically active substance may be any one selected from the group consisting of, for example, genistein, daidzein, cucurbitasin, prangenidin or a derivative thereof; a polyphenol; or a mixture thereof.

By way of example of the physiologically active substance, genistein, daidzein, cucurbitasin, prangenidin or a derivative thereof above, means a phenolic compound or a glycoside thereof contained in soybean, which has a structure similar to estrogen of a female hormone, and an excellent antioxidant effect, and the like, so that is used in various applications from skin care to anticancer treatment.

Specifically, the isoflavone may be genistein or a glycoside of the genistein, for example acetyl genistein or malonyl genistein, and the like, but is not limited thereto.

Isoflavone such as genistein, daidzein, cucurbitasin, prangenidin or a derivative thereof above is a phenolic compound, which includes intramolecular —H, wherein the intramolecular —H may form a hydrogen bond with a functional group being capable of forming the hydrogen bond contained in the second block (B) of the amphiphilic polymer to improve stability of the drug located inside the micelle.

The drug contained in the micelle may be included in an amount such that the physiological activity may be expressed, when the micelle has been prepared in a formulation.

In one example, the content of the drug may be in a range of 1 to 60% by weight, 1 to 50% by weight, 1 to 40% by weight or 1 to 20% by weight relative to the total weight of the micelle. When the content of the drug exceeds 60% by weight, the effective loading cannot be achieved, and the drug may be effused out of the micelle to be agglomerated into a crystal form or modified.

Such a micelle may have an average particle diameter in a range of 1 nm to 10,000 nm. The average particle diameter of the micelle is a value measured by a dynamic light scattering method, which may be a range covering a particle diameter of a single micelle or micelle aggregates themselves.

The micelle of the present application comprises the amphiphilic polymer encapsulating the drug.

The amphiphilic polymer of the present application comprises a first block (A) and a second block (B) that is phase-separated with the first block (A), and also the second block (B) comprises a polymerization unit (B1) of an acrylic monomer or a vinylic monomer having a solubility parameter of a single polymer of less than 10.0 $(cal/cm^3)^{1/2}$.

The amphiphilic polymer of the present application may include two blocks which are phase-separated from each other to effectively load a drug.

The term "phase-separated from each other" in the present application means a state that the first block and the second block are not mixed with each other in the absence of external action to form each block.

The amphiphilic polymer of the present application comprises the first block (A) and the second block (B) that is phase-separated with the first block (A).

The first block (A) means a hydrophilic area of the amphiphilic polymer, which may comprise, for example, a polymer having a solubility parameter of 10 $(cal/cm^3)^{1/2}$ or more.

Methods to obtain the solubility parameter are not particularly limited, and may follow methods known in the art. For example, the parameter may be calculated or obtained according to the method known in the art as so-called HSP (Hansen solubility parameter).

In another example, the first block (A) may comprise a polymer having a solubility parameter of has a solubility parameter of 13 $(cal/cm^3)^{1/2}$ or more, 14 $(cal/cm^3)^{1/2}$ or more, 15 $(cal/cm^3)^{1/2}$ or more, 16 $(cal/cm^3)^{1/2}$ or more or 17 $(cal/cm^3)^{1/2}$ or more. The upper limit of the solubility parameter of the first block (A) is not particularly limited, and may be, for example, 25 $(cal/cm^3)^{1/2}$ or less, or 23 $(cal/cm^3)^{1/2}$ or less.

The first block (A) may comprise the known polymers without any limitation, if they satisfy the abovementioned solubility parameter and may form a hydrophilic area of the amphiphilic polymer being capable of including a drug, according to the present invention.

In one example, the first block (A) may be any one selected from the group consisting of polyethylene glycol, a polyethylene glycol-propylene glycol copolymer, polyvinyl pyrrolidone and polyethyleneimine.

Specifically, the first block (A) may be polyethylene glycol having a number average molecular weight in a range of 500 to 100,000, but is not limited thereto. The term "number average molecular weight" in the present application may mean an analytical value measured by a nuclear magnetic resonator (NMR), and unless particularly specified otherwise, the molecular weight of any polymer may mean a number average molecular weight of the polymer.

The second block (B) comprises a polymerization unit (B1) of an acrylic monomer or a vinylic monomer having a solubility parameter of a single polymer of less than 10.0 $(cal/cm^3)^{1/2}$.

In the present application the term "acrylic monomer" means (meth)acrylic acid or a derivative thereof. In addition, the term "(meth)acrylic acid" means acrylic acid or methacrylic acid.

The second block (B) of the amphiphilic polymer of the present application is a site that serves to form a micelle shape by adjoining the drug and encapsulating around the drug.

Thus, the second block (B) refers to the relatively hydrophobic site within the amphiphilic polymer.

In another example, the second block (B) may comprise a polymerization unit (B1) of an acrylic monomer or a vinylic monomer having a solubility parameter of a single polymer of less than 9.8 $(cal/cm^3)^{1/2}$ or less than 9.5 $(cal/cm^3)^{1/2}$. The lower limit of the solubility parameter of the acrylic monomer or the vinylic monomer is not particularly limited, and may be, for example, 2 $(cal/cm^3)^{1/2}$ or more, or 4 $(cal/cm^3)^{1/2}$ or more.

As the acrylic monomer, a compound may be illustrated, which is represented by Formula 1 or 2 below, without being limited thereto.

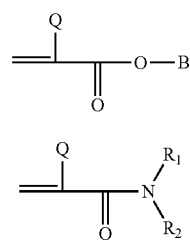

[Formula 1]

[Formula 2]

In Formulas 1 and 2, Q is hydrogen or an alkyl group, B in Formula 1 is a straight or branched alkyl group having at least one carbon atom, an alicyclic hydrocarbon group, an aromatic substituent or a carboxyl group, and $R_1$ and $R_2$ in Formula 2 are each independently hydrogen, a linear or branched alkyl group having at least one carbon atom, an alicyclic hydrocarbon group, or an aromatic substituent.

In Formulas 1 and 2, the alkyl group present in Q may use an alkyl group of 1 to 20 carbon atoms, 1 to 16 carbon atoms, 1 to 12 carbon atoms, 1 to 8 carbon atoms or 1 to 4 carbon atoms. The alkyl group may be of straight-chain, branched-chain or cyclic. In addition, the alkyl group may be optionally substituted by one or more substituents.

In Formulas 1 and 2, B, $R_1$ and $R_2$ may be each independently a straight or branched alkyl group of at least 1 carbon atom, at least 3 carbon atoms, at least 5 carbon atoms, at least 7 carbon atoms or at least 9 carbon atoms, which may be substituted or un-substituted. The compound comprising such a relatively long-chain alkyl group is known as a hydrophobic compound. The upper limit of the number of carbon atoms in the straight-chain or branched-chain alkyl group is not particularly limited, and for example, the alkyl group may be an alkyl group having up to 20 carbon atoms.

In Formulas 1 and 2, B, $R_1$ and $R_2$ may be, in another example, an alicyclic hydrocarbon group, for example, an alicyclic hydrocarbon group of 3 to 20 carbon atoms, 3 to 16 carbon atoms or 6 to 12 carbon atoms, and examples of such a hydrocarbon group may include an alicyclic alkyl group of 3 to 20 carbon atoms, 3 to 16 carbon atoms or 6 to 12 carbon atoms, and the like, such as a cyclohexyl group or an isobornyl group. The compound having such an alicyclic hydrocarbon group is also known as a relatively hydrophobic compound.

In Formulas 1 and 2, B, $R_1$ and $R_2$ may be, in another example, an aromatic substituent, for example, an aryl group or an arylalkyl group, and the like.

The aryl group above may be, for example, an aryl group of 6 to 24 carbon atoms, 6 to 18 carbon atoms or 6 to 12 carbon atoms. In addition, the alkyl group of the arylalkyl may be, for example, an alkyl group of 1 to 20 carbon atoms, 1 to 16 carbon atoms, 1 to 12 carbon atoms, 1 to 8 carbon atoms or 1 to 4 carbon atoms. As the aryl group or arylalkyl group a phenyl group, a phenylethyl group, a phenylpropyl group or a naphthyl group may be illustrated, without being limited thereto.

In Formulas 1 and 2 above herein, as a substituent being capable of being optionally substituted on the alkyl group, the aryl group or the hydrocarbon group, halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkenyl group, an alkynyl group or an aryl group, and the like, may be illustrated, without being limited thereto.

The compound represented by Formula 1 above may be, for example, alkyl (meth)acrylate. The term "(meth)acrylate" above refers to acrylate or methacrylate. The alkyl (meth)acrylate may include, for example, methyl (meth) acrylate, ethyl (meth)acrylate, n-propyl (meth)acrylate, isopropyl (meth)acrylate, n-butyl (meth)acrylate, t-butyl (meth) acrylate, sec-butyl (meth)acrylate, pentyl (meth)acrylate, hexyl (meth)acrylate, 2-ethylhexyl (meth)acrylate, 2-ethylbutyl (meth)acrylate, n-octyl (meth)acrylate, isobornyl (meth)acrylate, isooctyl (meth)acrylate, isononyl (meth) acrylate or lauryl (meth)acrylate, and the like, but is not limited thereto.

In the present application the appropriate type may be selected among monomers as above, considering the desired physical properties of amphiphilic polymers and used.

In one example, Q in Formula 1 above may be hydrogen or an alkyl group of 1 to 4 carbon atoms, and B may be an alkyl group of at least 7 carbon atoms or an alicyclic hydrocarbon group of 6 to 12 carbon atoms, without being limited thereto.

The second block (B) may comprise a polymerization unit (B1) of a vinylic monomer having a solubility parameter of a single polymer of less than 10 $(cal/cm^3)^{1/2}$.

The vinylic monomer may be, for example, a compound represented by Formula 3 or 4 below.

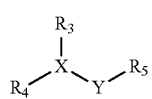

[Formula 3]

where, X is a nitrogen atom or an oxygen atom, Y is a carbonyl group or a single bond, $R_3$ and $R_5$ are each independently hydrogen or an alkyl group, or $R_3$ and $R_5$ are linked together to form an alkylene group, and $R_4$ is an alkenyl group (provided that $R_3$ is not present, if X is an oxygen atom);

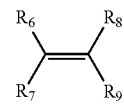

[Formula 4]

where, $R_6$, $R_7$ and $R_8$ are each independently hydrogen or an alkyl group, and $R_9$ is a cyano group or an aromatic substituent.

When Y in Formula 3 is a single bond, no separate atom is present in the portion indicated by Y, and a structure directly linking $R_5$ and X may be established.

In Formula 3, $R_4$ may be, for example, a straight, branched or cyclic alkenyl group of 2 to 20 carbon atoms, 2 to 16 carbon atoms, 2 to 12 carbon atoms, 2 to 8 carbon atoms or 2 to 4 carbon atoms, which may be optionally substituted or un-substituted. Generally, as the alkenyl group a vinyl group or an aryl group, and the like may be used.

In Formula 3, $R_3$ and $R_5$ may be each independently hydrogen or a straight, branched or cyclic alkyl group of 1 to 20 carbon atoms, 1 to 16 carbon atoms, 1 to 12 carbon atoms, 1 to 8 carbon atoms or 1 to 4 carbon atoms, or linked together to form an alkylene group of 1 to 20 carbon atoms, 2 to 16 carbon atoms, 2 to 12 carbon atoms or 2 to 8 carbon atoms. When $R_3$ and $R_5$ above form an alkylene group, the compound of Formula 3 may be a cyclic compound.

As the vinylic monomer represented by Formula 3 or 4 above, a styrenic monomer such as styrene, or methyl styrene; acrylonitrile; an amide-based monomer such as N-vinyl amide compound; an ester-based monomer such as vinyl ester compound; or an ether-based monomer such as vinyl ether compound; and the lie, may be illustrated, without being limited thereto, and if the monomer satisfies the aforementioned solubility parameter of a single polymer, it may be used as the vinylic monomer contained as a polymerization unit in the amphiphilic polymer of the present application, without any limitation.

In addition, the second block (B) may further comprise, in addition to the aforementioned polymerization unit (B1) of the acrylic monomer or the vinylic monomer, a polymerization unit (B2) of a polymerizable monomer having a functional group being capable of forming a hydrogen bond.

The amphiphilic polymer of the present application may improve the loading ability for the targeted drug and stably locate in the inside (core) of the micelle, by including the aforementioned polymerization unit (B1) of the acrylic monomer or the vinylic monomer and the polymerization unit (B2) of the polymerizable monomer having a functional group being capable of forming a hydrogen bond in the second block (B) at the same time.

The polymerizable monomer having a functional group being capable of forming a hydrogen bond above is a polymerizable monomer except for the above-mentioned acrylic monomers and vinyl monomers, which may refer to a monomer having a functional group being capable of forming a hydrogen bond.

In one example, as the functional group of the polymerizable monomer, a hydroxy group, an amine group, a nitro group, an amino group, an imide group, an alkoxysilane group or a cyano group, and the like may be illustrated, without being limited thereto, and if it is a functional group serving as an electron donor which may improve the loading ability of drugs by forming an interaction with —H, specifically a hydrogen bond, in the drug to be described later and more stably locate the drug in the inside (core) of the micelle, there is no limitation.

As the polymerizable monomer containing an amine group, for example, 2-aminoethyl (meth)acrylate, 3-aminopropyl (meth)acrylate, N,N-dimethylaminoethyl (meth) acrylate or N,N-dimethylaminopropyl (meth)acrylate, and the like may be illustrated, without being limited thereto.

As the polymerizable monomer containing an alkoxysilane group, for example, vinyl alkoxysilane, allyl alkoxysilane, (meth)acryloxyalkyl alkoxysilane or vinylacryloxysilane, and the like may be illustrated. In addition, the (meth) acryloxyalkyl alkoxysilane may include, for example, 3-(meth)acryloxypropyl methyldimethoxysilane, 3-(meth) acryloxypropyl methyldiethoxysilane, 3-(meth)acryloxy trimethoxysilane, 3-(meth)acryloxypropyl triethoxysilane, (meth)acryloxymethyl triethoxysilane or (meth)acryloxymethyl tris(trimethylsiloxy)silane, and the like, but is not limited thereto.

As the polymerizable monomer containing a cyano group, for example, cyanomethyl (meth)acrylate, cyanoethyl (meth)acrylate or cyanopropyl (meth)acrylate, and the like may be illustrated, without being limited thereto.

Such a polymerizable monomer having a functional group being capable of forming a hydrogen bond forms a polymerization unit (B2) to the second block (B), and the polymerization units (B2) is located, for example, on the outside of the polymer, so that it may serve for loading the drug.

In addition, the second block (B) may comprise the aforementioned polymerization unit (B1) of the acrylic monomer or the vinylic monomer and the polymerization unit (B2) of the polymerizable monomer having a functional group being capable of forming a hydrogen bond in a predetermined weight ratio.

For example, the weight ratio (B1:B2) of the polymerization unit (B1) of the acrylic monomer or the vinylic monomer having a solubility parameter of a single polymer of less than 10.0 $(cal/cm^3)^{1/2}$ and the polymerization unit (B2) of the polymerizable monomer having a crosslinkable functional group being capable of forming a hydrogen bond, in the second block (B), may be the same or different. For example, the weight ratio (B1:B2) may be in a range of 1:9 to 9:1. In another example, the weight ratio (B1:B2) may be in a range of 2:8 to 8:2, 3:7 to 7:3 or 4:6 to 6:4. In the range of such a weight ratio (B1:B2), the drug may be effectively loaded, and the amphiphilic polymer safely dispersed in an aqueous solution may be formed.

The second block (B) may have, for example, a number average molecular weight in a range of 500 to 100,000. In such a range, the desired hydrophobic properties and loading ability for the drug may be secured.

In the amphiphilic polymer of the present application, the block ratio (A:B) of the first block (A) and the second block (B) may be the same or different.

In one example, the amphiphilic polymer may have a different block ratio (A:B) of the first block (A) and the second block (B).

Specifically, in the amphiphilic polymer of the present application the block ratio (A:B) of the first block (A) and the second block (B) may be adjusted in a range of 1:9 to 9:1. The term block ratio (A:B) above refers to the weight ratio between the respective blocks.

In another example, the block ratio (A:B) of the first block (A) and the second block (B) may be 2:8 to 8:2, 3:7 to 7:3 or 4:6 to 6:4.

In the range of such a block ratio (A:B), the desired dispersion property may be effectively secured, and also the percutaneous absorption characteristic of the formulation may be improved.

The amphiphilic polymer may have a number average molecular weight (Mn) in a range of 1,000 to 500,000.

The micelle according to the present application may have a different block ratio (A:b) of the first block (A) and the second block (B), as described above, and also include the amphiphilic polymer comprising a functional group allowing for a certain interaction with the drug to have an excellent encapsulation characteristic, a dispersion property in an aqueous solution and a superior percutaneous absorption characteristic, and the like.

The present application relates also to a composition comprising such micelles.

In one example, the present application relates to a composition for preparing particles comprising a drug and a micelle comprising the amphiphilic polymer encapsulating the drug.

The composition for preparing particles of the present application comprises a micelle formed due to the self assembly characteristic of the amphiphilic polymer. In addition, such amphiphilic polymers forming the micelle encapsulate, for example, the drug.

In addition, the present application relates to a pharmaceutical or cosmetic composition comprising the micelles comprising the amphiphilic polymer.

Specifically, the micelle contained in the pharmaceutical or cosmetic composition comprises an amphiphilic polymer and a drug that is encapsulated by the amphiphilic polymer.

In one example, if the composition is a pharmaceutical composition, the drug in the micelle can be included in the composition as a pharmaceutically acceptable form. In addition, the pharmaceutical composition may further comprise a pharmaceutically acceptable carrier.

In addition, the pharmaceutical composition may be in various oral or parenteral dosage forms.

When the pharmaceutical composition is formulated, it may be prepared using diluents or excipients, such as fillers, extenders, binders, humectants, disintegrators and surfactants, as commonly used.

In one example, a solid formulation for oral administration includes tablets, pills, powders, granules, or capsules, and such a solid formulation may be prepared by mixing one or more compounds at least with one or more excipients, for example, starch calcium carbonate, sucrose or lactose, gelatin, and the like.

In one example, a liquid formulation for oral administration corresponds to suspensions, internal solutions, emulsions, or syrups and the like, in which various excipients, for example, wetting agents, sweeteners, aromatics, or preservatives, and the like may be included, other than water or liquid paraffin as the commonly used simple diluents. A formulation for parenteral administration may include sterile aqueous solutions, non-aqueous solvents, suspensions, emulsions, lyophilized formulations, or suppositories.

The pharmaceutical composition may be formulated in any form suitable for pharmaceutical preparations, including oral dosage forms such as powders, granules, tablets, capsules, suspensions, emulsions, syrups, or aerosols; external preparations such as ointments or creams; suppositories; sterile injection solutions, and the like, in accordance with each conventional method.

In another example, the composition may be a cosmetic composition that can be included in external preparations for skin having formulations, for example, emollients, astringent lotions, nourishing lotions, nourishing creams, cleansing foams, essences, packs, and the like.

In the cosmetic compositions and external preparations for skin, the known additive components, for example, powdery bases or carriers (binders, disintegrators, excipients or lubricants and the like), oily bases or carriers (animal and vegetable oils, waxes, Vaseline, paraffin oils, silicone oils, higher fatty acid esters or higher fatty acids, etc.), aqueous bases or carriers (gel bases, such as xanthan gum), preservatives, chelating agents, antioxidants, algefacients, stabilizers, fluidizers, emulsifiers, thickeners, buffering agents, dispersing agents, absorbents, moisturizing agents, wetting agents, desiccants, antistatic agents or other resins (polyamide-based resins, olefinic resins such as hydrogenated polybutene, etc.), and the like may be included.

Such a pharmaceutical composition or cosmetic composition may be in a water-in-oil type or oil-in-water type of emulsion form.

The micelle in the composition may form, for example, aggregates. Such micelle aggregates may be formed due to van der Waals force between the hydrophobic areas or the like. The size of such micelle aggregates may be, for example, in a range of 10 nm to 10,000 nm.

The present application relates also to a process for preparing the aforementioned micelle.

That is, the present application relates to a process for preparing the micelle comprising a step of polymerizing a polymer forming a first block (A) and an acrylic monomer or a vinylic monomer having a solubility parameter of a single polymer of less than 10.0 $(cal/cm^3)^{1/2}$ to prepare an amphiphilic polymer; and a step of mixing the amphiphilic polymer and a drug.

Specifically, in the process for preparing the amphiphilic polymer of the present application, the method of polymerizing the polymer forming the first block (A) and the aforementioned monomer is not particularly limited, but may utilize a living radical polymerization, for example, atom transfer radical polymerization (ATRP) for effectively achieving narrow molecular weight distribution and the desired molecular weight.

More specifically, the amphiphilic polymer of the present application may be prepared by reacting a polymer which comprises a halogen atom and forms the first block (A) with a transition metal complex catalyst to generate a radical, and giving such a radical with an electron from a double bond site of the acrylic monomer or the vinylic monomer for forming the second block to form the second block (B) having the polymerization unit (B1) of the acrylic monomer or the vinylic monomer, but is not limited thereto.

The polymer forming the first block is, for example, a polymer, with or without a halogen atom, having a solubility parameter of 10 $(cal/cm^3)^{1/2}$ or more, and when the polymer without a halogen atom for forming the first block is used, a step of preparing an initiator for ATRP through a reaction with a compound containing a halogen atom may be further included.

The step of mixing the amphiphilic polymer prepared as above with a drug may comprise, for example, dissolving the amphiphilic polymer in a certain organic solvent, for example ethanol, and the like, and then mixing the prepared solution and the drug.

In addition, after the above process, the subsequent process may include a process of removing the solvent, without being limited thereto, and the known further process may be entailed between the processes above or to the subsequent process.

The temperature in the step of removing the solvent varies depending on the boiling point of each solvent, and for example, the solvent may be removed at a temperature of 50° C. or more, but is not limited thereto.

Effect of the Invention

The present application may provide the micelles which are effectively dispersed in the composition and comprise the drug encapsulated by the amphiphilic polymer having high stability for the drug, and the process for preparing the same.

In addition, the formulation containing such micelles can exhibit excellent percutaneous absorption properties.

BRIEF DESCRIPTION OF DRAWINGS

FIG. 1 is a schematic view about the micelle comprising the amphiphilic polymer according to the present application.

FIG. 2 is images confirming precipitation of the amphiphilic polymer according to Examples and Comparative Examples and the drug encapsulated by the polymer through an optical microscope.

FIG. 3 is a schematic view about a Franz cell for the percutaneous absorption experiment.

DETAILED DESCRIPTION OF THE INVENTION

Hereinafter, the present application will be explained in more detail through Examples, but the Examples are restricted only to the gist of the present application. Furthermore, the present application is not limited to the process conditions suggested in the following Examples, and it is obvious to those having ordinary knowledge in the art that it can be optionally selected within the range of conditions necessary for achieving the object of the present application.

EXAMPLES

Example 1—Preparation of Amphiphilic Polymer (P1)

After dissolving a polyethylene glycol monomethyl ether polymer (molecular weight: 5,000, manufacturer: Aldrich) forming the first block in dichloromethane with a 30% concentration, 3 equivalents of triethylamine and 2 equivalents of 2-bromoisobutyryl bromide are added, relative to the —OH functional group, and reacted to prepare the initiator for ATRP. Then, the precipitation and loading process is twice repeated in diethyl ether solvent and dried to obtain the polyethylene glycol polymer having bromine terminals without impurities. 100 parts by weight of the obtained polyethylene glycol polymer having bromine terminals was dissolved in 250 parts by weight of anisole reaction solvent on a flask, 150 parts by weight of methyl methacrylate (solubility parameter: 9.5 $(cal/cm^3)^{1/2}$), and the flask was sealed with a rubber stopper. Then, the dissolved oxygen was removed through nitrogen purging and stirring at room temperature for 30 minutes, and the reaction was progressed by dipping it in an oil bath set to 60° C. and introducing a cupric bromide complex and a catalyst reducing agent. If the desired molecular weight was obtained, the reaction was completed to prepare the amphiphilic polymer (PI). The molecular weight and block ratio (A:B) of the amphiphilic polymer (P1) are shown in Table 1 below.

Example 2—Preparation of Amphiphilic Polymer (P2)

The amphiphilic polymer (P2) was prepared in the same manner as Example 1 except that the polyethylene glycol polymer having bromine terminals as prepared in the same manner as Example 1 was dissolved in the anisole reaction solvent on the flask, and methyl methacrylate (solubility parameter: 9.5 $(cal/cm^3)^{1/2}$) and N,N-dimethylaminoethyl methacrylate (solubility parameter: 9.6 $(cal/cm^3)^{1/2}$) were introduced in a weight ratio of 80:20. The molecular weight and block ratio (A:B) of the amphiphilic block polymer (P2) and the weight ratio (B1:B2) of polymerization units in the second block (B) are shown in Table 1 below.

Example 3—Preparation of Amphiphilic Polymer (P3)

The amphiphilic polymer (P3) was prepared in the same manner as Example 1 except that the polyethylene glycol polymer having bromine terminals as prepared in the same manner as Example 1 was dissolved in the anisole reaction solvent on the flask, and methyl methacrylate (solubility parameter: 9.5 $(cal/cm^3)^{1/2}$) and N,N-dimethylaminoethyl methacrylate (solubility parameter: 9.6 $(cal/cm^3)^{1/2}$) were introduced in a weight ratio of 60:40. The molecular weight and block ratio (A:B) of the amphiphilic block polymer (P3) and the weight ratio (B1:B2) of polymerization units in the second block (B) are shown in Table 1 below.

Comparative Example 1—Preparation of Amphiphilic Polymer (P4)

The polyethylene glycol (A)-polycaprolactone (B) copolymer (P4) applied by polycaprolactone (solubility parameter: about 10 $(cal/cm^3)^{1/2}$) being a polyester-based polymer, was prepared by the following method.

Specifically, it was synthesized via a ring-opening polymerization using polyethyleneglycol monomethyl ether polymer (molecular weight: 5000, manufacturer: Aldrich) as an initiator. Stannous 2-ethyl-hexanoate ($Sn(Oct)_2$) was used as a reaction catalyst. Polyethylene glycol monomethyl ether and $Sn(Oct)_2$ were dried in a 2-neck round flask at 110° C. for 4 hours under vacuum to remove water and then, the reactor was cooled to room temperature. Polyethyleneglycol monomethyl ether and the same amount of ε-caprolactone were added to the reactor in a nitrogen atmosphere and vacuum dried for 1 hour at 60° C. The reactor was gradually raised to 130° C. in a nitrogen atmosphere, reacted for 18 hours, and the reaction was terminated by cooling to room temperature. Methylene chloride was added to the reactor cooled to room temperature to dissolve the reactant, and then the copolymer was precipitated while slowly adding it to the cold ethyl ether. The precipitated block copolymer was filtered and then vacuum dried at 40° C. for 48 hours to finally obtain the polyethylene glycol (A)-polycaprolactone (B) copolymer (P4).

Comparative Example 2—Preparation of Amphiphilic Polymer (P5)

The amphiphilic polymer (P5) was synthesized and prepared in the same manner as Comparative Example 1 except that on synthesizing the polyethylene glycol (A)-polycaprolactone (B) copolymer applied by polycaprolactone (solubility parameter: about 10 $(cal/cm^3)^{1/2}$) being a polyester-based polymer two-fold amount of ε-caprolactone was added, relative to polyethyleneglycol monomethyl ether.

Experimental Example 1—Evaluation of Block Ratio (A:B) and Molecular Weight of the Prepared Amphiphilic Polymers Block ratios and molecular weights of the prepared amphiphilic polymers (P1 to P5) were evaluated by the following method and shown in Table 1.

Specifically, the polymer solution completely removing the catalyst was solidified via the purification step, and then the block ratio of the amphiphilic polymer was confirmed through $^1H$ NMR analysis. In the purification of the polymer solution, the polymer solution is passed through an alumina column to remove the copper complex catalyst and then falls in drops to an excess of diethyl ether with stirring to remove the residual monomer, and is solidified. The solidified polymer is dried for 24 hours in a vacuum oven. The amphiphilic polymer purified by the above method is dissolved in $CDCl_3$ solvent and measured by $^1H$-NMR analysis equipment. In the case of Examples 1 to 3, from the analyzed result, no 1H peaks derived from $CH_2=C(CH_3)$— of the double bond terminal were confirmed, whereby it can be confirm that the unreacted monomer is not present. In addition, in the case of Examples 1 to 3 and Comparative Examples 1 and 2, 3H peaks derived from —$OCH_3$ of the ethylene glycol block terminal were identified near 3.2 ppm and on the base of this, the ratio and molecular weight of each polymer block was calculated. Since about 450 of H peaks (4H×113 repeating units) derived from —$CH_2CH_2O$— of ethylene glycol forming the polymer appeared in the region of 3.6 to 3.8 ppm, 3H peaks derived from —$CH_3$ adjacent to the backbone of methyl methacrylate forming the polymer in the case of Examples 1 to 3 appeared in the region of 3.5 to 3.6 ppm, and 2H peaks derived from —$OCH_2$— adjacent to —COO— of the dimethylamonoethyl methacrylated side chain forming the polymer appeared in the region of 4.0 to 4.2 ppm, the contents of the constituent monomers each were calculated as a mass fraction through their area ratios. Since 2H peaks derived from the first right —$CH_2$— of —CO— in —(CO—$CH_2CH_2CH_2CH_2CH_2$—O—) n being the chain of caprolactone forming the polymer in the case of Comparative Examples 1 and 2, appeared in the region of 2.3 to 2.4 ppm, the molecular weight was identified through the 3H peak area derived from —$OCH_3$ of the ethylene glycol block terminal and the 2H peak area derived from the first right —$CH_2$— of —CO— in caprolactone.

TABLE 1

| | Molecular weight (Mn, first block: second block) | Block ratio (A:B) | Weight ratio of polymerization unit in second block (B) (B1:B2)a |
|---|---|---|---|
| Example 1 | 11,000 (5,000:6,000) | 4.55:5.45 | 100:0 |
| Example 2 | 11,000 (5,000:6,000) | 4.55:5.45 | 80:20 |
| Example 3 | 11,000 (5,000:6,000) | 4.55:5.45 | 60:40 |
| Comparative Example 1 | 9,900 (5,000:4,900) | 5.05:4.95 | — |
| Comparative Example 2 | 14,700 (5,000:9,700) | 0.34:0.66 | — | a: methyl methacrylate (B1):N,N-dimethylaminoethyl methacrylate (B2) mass ratio

Experimental Example 2—Preparation of Micelle and Determination of Dissolved Concentration of Drug Using the synthesized amphiphilic polymers (P1 to P5), genistein of a sparingly soluble material was encapsulated. First, a solution of the amphiphilic polymer (10 g) dissolved in 30 mL of ethanol was mixed with a solution of genistein (2 g) dissolved in 20 g of dipropylene glycol (DPG). The solution was slowly added to 100 mL of 0.5% aqueous polyvinyl alcohol solution while stirring. After standing the solution for a certain time with stirring in order to evaporate the ethanol solvent, the remaining ethanol was removed using a rotary evaporator to prepare a solution such that the content of genistein is 2%. The prepared solution was diluted with purified water of ten times and then stored at room temperature (25° C.) for 7 days, where it was confirmed with an optical microscope whether the change over time was and shown in FIG. 2. In addition, the liquid was filtered through a syringe filter (pore size: 1 µm) to remove the precipitated genistein and then the content of the genistein encapsulated in the amphiphilic polymer micelle particles was measured from a liquid chromatography (HPLC). Drug loading capacity and drug loading efficiency of the amphiphilic polymer were calculated by the following equations, and the particle size of the micelle comprising the amphiphilic polymer loading the drug was measured using Zetasizer 3000 from Malvern Instruments.

$$\text{Drug loading capacity} = \frac{\text{Drug impregnation amount}}{\text{Drug impregnation amount} + \text{Block copolymer content}} \times 100(\%) \quad [\text{Equation 1}]$$

$$\text{Drug loading efficiency} = \frac{\text{Drug impregnation amount}}{\text{Initial drug input amout}} \times 100(\%) \quad [\text{Equation 2}]$$

The results measuring the size of the micelle particles, and drug loading capacity and drug loading efficiency according to these were showed in Table 2 below.

TABLE 2

|  | Example 1 | Example 2 | Example 3 | Comparative Example 1 | Comparative Example 2 |
|---|---|---|---|---|---|
| Particle Size (nm) | 110 | 125 | 135 | 100 | 150 |
| Drug loading capacity (%) | 2.4 | 10.7 | 16.1 | 1.2 | 1.8 |
| Drug loading efficiency (%) | 13 | 60 | 96 | 6 | 9 |

Experimental Example 3—Percutaneous Absorption Experiment

The percutaneous absorption of genistein was evaluated from the above prepared amphiphilic polymer solution loading genistein us porcine skin (2×2 cm, thickness 1000 µm) and Franz diffusion cell. The sink condition for genistein was maintained using the PBS (phosphate buffered saline) solution containing 30% by weight of dipropylene glycol (DPG) as an acceptor solution. After loading 0.2 g of the amphiphilic polymer solution loading genistein on the Franz diffusion cell equipped with the porcine skin, the experiment was carried out at 32° C. similar to the skin temperature for 24 hours. The skin tissues absorbing genistein were crushed and extracted to analyze the genistein content absorbed in the skin tissues and the genistein content in the acceptor solution through HPLC, which were shown in Table 3.

TABLE 3

|  | Example 1 | Example 2 | Example 3 | Comparative Example 1 | Comparative Example 2 |
|---|---|---|---|---|---|
| Skin permeation amount (µg/cm$^2$) | 0.66 | 1.85 | 3.70 | 0.22 | 0.35 |
| Skin permeability (%) | 0.38 | 1.05 | 2.10 | 0.13 | 0.20 |

EXPLANATION OF CODES

100: Drug
200: Amphiphilic polymer
201: First block
202: Second block

What is claimed is:

1. A micelle comprising:
a drug; and
an amphiphilic polymer which encapsulates said drug, has a first block (A) and a second block (B) that is phase-separated with said first block (A) and comprises a polymerization unit (B1) of an acrylic monomer or a vinylic monomer having a solubility parameter of a single polymer of less than 10.0 (cal/cm$^3$)$^{1/2}$ and a polymerization unit (B2) of a polymerizable monomer having a functional group being capable of forming a hydrogen bond,
wherein the first block (A) comprises a polymer having a solubility parameter of 10 (cal/cm$^3$)$^{1/2}$ or more,
wherein a weight ratio (B1:B2) of the polymerization unit (B1) of an acrylic monomer or a vinylic monomer having a solubility parameter of a single polymer of less than 10.0 (cal/cm$^3$)$^{1/2}$ and the polymerization unit (B2) of a polymerizable monomer having a functional group being capable of forming a hydrogen bond, in the second block (B), is in a range of 1:9 to 9:1,
wherein the drug includes intramolecular —H, wherein the intramolecular —H forms a hydrogen bond with the functional group of polymerization unit (B2) in the second block (B) of the amphiphilic polymer.

2. The micelle according to claim 1, wherein the drug comprises a physiologically active substance.

3. The micelle according to claim 2, wherein the physiologically active substance is sparingly soluble.

4. The micelle according to claim 3, wherein the sparingly soluble and physiologically active substance is any one selected from the group consisting of genistein, daidzein, cucurbitasin, prangenidin or a derivative thereof; a polyphenol; or a mixture thereof.

5. The micelle according to claim 4, wherein the sparingly soluble and physiologically active substance is genistein or a glycoside of said genistein.

6. The micelle according to claim 1, wherein the first block (A) is any one selected from the group consisting of polyethylene glycol, a polyethylene glycol-propylene glycol copolymer, polyvinyl pyrrolidone and polyethyleneimine.

7. The micelle according to claim 1, wherein
the acrylic monomer is represented by Formula 1 or Formula 2 below:

[Formula 1]

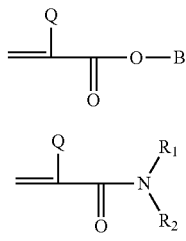

[Formula 2]

where, Q in Formula 1 and 2 is hydrogen or an alkyl group, B in Formula 1 is a straight or branched alkyl group having at least one carbon atom, an alicyclic hydrocarbon group, an aromatic substituent or a carboxyl group, and $R_1$ and $R_2$ in Formula 2 are each independently hydrogen, a straight or branched alkyl group having at least one carbon atom, an alicyclic hydrocarbon group, or an aromatic substituent.

8. The micelle according to claim 7, wherein
Q in Formula 1 is hydrogen or an alkyl group having 1 to 4 carbon atoms, B is an alkyl group having at least one carbon atom or an alicyclic hydrocarbon group having 6 to 12 carbon atoms.

9. The micelle according to claim 1, wherein
the vinylic monomer is represented by Formula 3 or Formula 4 below:

[Formula 3]

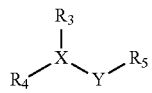

where, X is a nitrogen atom or an oxygen atom, Y is a carbonyl group or a single bond, $R_3$ and $R_5$ are each independently hydrogen or an alkyl group, or $R_3$ and $R_5$ are linked together to form an alkylene group, and $R_4$ is an alkenyl group (provided that $R_3$ is not present, if X is an oxygen atom);

[Formula 4]

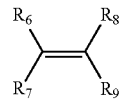

where, $R_6$, $R_7$ and $R_8$ are each independently hydrogen or an alkyl group, and $R_9$ is a cyano group or an aromatic substituent.

10. The micelle according to claim 1, wherein
the functional group is a hydroxyl group, an amine group, a nitro group, an amino group, an imide group, an alkoxysilane group or a cyano group.

11. The micelle according to claim 1, wherein
the amphiphilic polymer has a block ratio (A:B) of the first block (A) and the second block (B) different from each other.

12. The micelle according to claim 11, wherein
the block ratio (A:B) of the first block (A) and the second block (B) in the amphiphilic polymer is 1:9 to 9:1.

13. The micelle according to claim 1, wherein
the block ratio (A:B) of the first block (A) and the second block (B) in the amphiphilic polymer is 3:7 to 7:3.

14. The micelle according to claim 1, wherein
the second block of the amphiphilic polymer is adjacent to the drug.

15. The micelle according to claim 1, wherein
the average particle diameter is in a range of 1 to 10,000 nm.

16. A composition for preparing particles comprising the micelle of claim 1.

17. A pharmaceutical or cosmetic composition comprising the micelle of claim 1.

18. The pharmaceutical or cosmetic composition according to claim 17, wherein the composition is in a water-in-oil type emulsion form or an oil-in-water type emulsion form.

19. A process for preparing the micelle of claim 1 comprising:
a step of polymerizing a polymer forming a first block (A) and an acrylic monomer or a vinylic monomer having a solubility parameter of a single polymer of less than 10.0 $(cal/cm^3)^{1/2}$ to prepare an amphiphilic polymer; and
a step of mixing said amphiphilic polymer and a drug.

* * * * *